(12) United States Patent
Modarres

(10) Patent No.: US 6,993,380 B1
(45) Date of Patent: Jan. 31, 2006

(54) QUANTITATIVE SLEEP ANALYSIS METHOD AND SYSTEM

(75) Inventor: MoHammad Modarres, Cleveland Heights, OH (US)

(73) Assignee: Cleveland Medical Devices, Inc., Cleveland, OH (US)

( * ) Notice: Subject to any disclaimer, the term of this patent is extended or adjusted under 35 U.S.C. 154(b) by 74 days.

(21) Appl. No.: 10/454,156

(22) Filed: Jun. 4, 2003

(51) Int. Cl.
    *A61B 5/04* (2006.01)
(52) U.S. Cl. .................................... 600/544
(58) Field of Classification Search ............... 600/544, 600/545
    See application file for complete search history.

(56) References Cited

U.S. PATENT DOCUMENTS

| | | | |
|---|---|---|---|
| 5,520,176 A * | 5/1996 | Cohen | 600/300 |
| 5,595,488 A | 1/1997 | Gozlan et al. | |
| 5,626,145 A | 5/1997 | Clapp et al. | |
| 5,689,241 A | 11/1997 | Clarke, Sr. et al. | |
| 5,740,812 A | 4/1998 | Cowan | |
| 5,813,993 A * | 9/1998 | Kaplan et al. | 600/544 |
| 5,884,626 A | 3/1999 | Kuroda et al. | |
| 5,899,922 A | 5/1999 | Loos | |
| 6,059,725 A | 5/2000 | Steinschneider | |
| 6,070,098 A | 5/2000 | Moore-Ede et al. | |
| 6,154,123 A | 11/2000 | Kleinberg | |
| 6,167,298 A * | 12/2000 | Levin | 600/545 |
| 6,204,245 B1 | 3/2001 | Siegel et al. | |
| 6,241,686 B1 | 6/2001 | Balkin et al. | |
| 6,272,378 B1 | 8/2001 | Baumgart-Schmitt | |
| 6,292,688 B1 | 9/2001 | Patton | |
| 6,293,904 B1 | 9/2001 | Blazey et al. | |
| 6,313,749 B1 | 11/2001 | Horne et al. | |
| 6,353,396 B1 | 3/2002 | Atlas | |
| 6,434,419 B1 * | 8/2002 | Gevins et al. | 600/544 |
| 6,496,724 B1 * | 12/2002 | Levendowski et al. | 600/544 |
| 6,625,485 B2 * | 9/2003 | Levendowski et al. | 600/544 |
| 2003/0013981 A1 * | 1/2003 | Gevins et al. | 600/544 |

OTHER PUBLICATIONS

Makeig. Scott and Inlow, Mark, Lapses in Alertness: Coherance of Fluctuations in performance and EEG Spectrum. Electroencphalography and Clinical Neurophysiology, 1993 vol 86 pp 23-25 .

* cited by examiner

*Primary Examiner*—Charles Marmor
*Assistant Examiner*—Navin Natnithithadha
(74) *Attorney, Agent, or Firm*—Brian M. Kolkowski

(57) ABSTRACT

The present invention relates to a method of analyzing a subject for excessive daytime sleepiness, and more particularly to a quick (short duration), quantitative method of sleep disorder analysis. The present invention additionally relates to a method, which can be used to quantitatively measure the treatment endpoints for the subject, i.e., appropriate levels of stimulants. Additionally, the present invention relates to a device for sleep disorder analysis.

20 Claims, 3 Drawing Sheets

QUANTITATIVE SLEEP ANALYSIS METHOD AND SYSTEM

The U.S. Government has a paid-up license in this invention and the right in limited circumstances to require the patent owner to license others on reasonable terms provided for by the terms of grant numbers 5 R44 HL70327-03 and N43-NS-9-2307 awarded by the National Institutes of Health.

BACKGROUND OF THE INVENTION

1. Field of the Invention

The present invention relates to a method of analyzing a subject for excessive daytime sleepiness, and more particularly to a quick (short duration), quantitative method of sleep disorder analysis. The present invention additionally relates to a method, which can be used to quantitatively measure the treatment endpoints for the subject, i.e., appropriate levels of stimulants.

2. Technical Background

Nearly one in seven people in the United States suffer from some type of chronic sleep disorder, and only fifty percent (50%) of people are estimated to get the recommended seven (7) to eight (8) hours of sleep each night. It is further estimated that sleep deprivation and its associated medical and social costs (loss of productivity, industrial accidents, etc) exceed $150 billion dollars per year. Excessive sleepiness can deteriorate the quality of life and is a major cause of morbidity and mortality due to its role in industrial and transportation accidents. Sleepiness further has undesirable effects on motor vehicle driving, employment, higher earning and job promotion opportunities, education, recreation, and personal life.

Excessive daytime sleepiness (EDS) is a symptom describing an increased propensity to fall asleep, often during monotonous or sedentary activities. Though sometimes difficult, EDS vs. fatigue need to be differentiated. Fatigue or lethargy is where a subject senses a lack of energy or physical weakness and may not have an increased propensity to fall asleep at an inappropriate time. The underlying etiology of EDS generally falls into three categories: chronic sleep deprivation, circadian disorders (shift work), and sleep disorders. EDS is currently diagnosed via two general methods. The first is via subjective methods such as the Epworth and Standford Sleepiness Scale, which generally involves questionnaires where the patients answer a series of qualitative questions regarding their sleepiness during the day. With these methods, however, it is found that the patients usually underestimate their level of sleepiness or they deliberately falsify their responses because of their concern regarding punitive action, or as an effort to obtain restricted stimulant medication.

The second is via physiological based evaluations such as all night polysomnography to evaluate the patients sleep architecture (e.g., obtaining respiratory disturbance index to diagnose sleep apnea) followed by an all day test such as the Multiple Sleep Latency Test (MSLT) or its modified version, Maintenance of Wakefulness Test (MWT). The MSLT consists of four (4) to five (5) naps and is considered the most reliable objective measure of sleepiness to date. The MSLT involves monitoring the patient during twenty (20) to fourty (40) minute nap periods in two-hour intervals one and one half hour (1.5 hrs) to three hours (3 hrs) after awakenings to examine the sleep latency and the sleep stage that the patient achieves during these naps, i.e., the time it takes for the patient to fall asleep. A sleep disorder such as narcolepsy for example is diagnosed when the patient has a restful night sleep the night before but undergoes rapid eye movement sleep (REM sleep) within five (5) minutes of the MSLT naps. The MWT is a variation of the MSLT. The MWT provides an objective measure of the ability of an individual to stay awake.

While the MSLT and MWT are more objective and therefore don't have the same limitations as mentioned for the subjective tests, the MSLT and MWT have their own limitations. Both the MSLT and MWT require an all-day stay at a specialized sleep clinic and involve monitoring a number of nap opportunities at two hour intervals throughout the day. Further, the MSLT mean sleep latency is only meaningful if it is extremely short in duration (e.g., to diagnose narcolepsy), and only if the overnight polysomnogram does not show any sleep disordered breathing. Another problem with the MSLT mean sleep latency is the so-called "floor effect" where the sleep latency in the pathologically sleepy patients can be almost zero (0) minutes, i.e., the patient falls asleep almost immediately following turning off the light in the MSLT test. This type of result has a tendency to limit the diagnostic resolution of the test. Finally, studies have shown that the MSLT is not particularly suited for gauging the effects of therapeutic intervention. This was demonstrated in studies by Thorpy in 1992 and Van den Hoed et al. in 1981 showing no reliable reduction in sleepiness in patients given stimulant medications for narcolepsy.

The MWT was developed in 1982, in part, to address some of the short-comings of the MSLT method. The MWT eliminated the "floor effect" in the MSLT test shown in narcoleptic patients due to the instruction in the MWT test to the patient to stay awake. The MWT, however, created another problem at the other end of the sleep latency period called the "ceiling effect". The "ceiling effect" is the tendency of less "sleepy" individuals to perform the MWT without falling asleep. In fact, the length of the MWT trial was lengthened from twenty (20) to fourty (40) minutes in 1984 because it was observed that patients with histories of excessive daytime sleepiness were too often able to maintain wakefulness for the twenty (20) minutes. In addition, while the MSLT and MWT are objective and "broadly" quantitative tests in that they both require the patient to fall asleep during the test and they measure the number of those incidents of sleep during the testing regiment, these tests are too costly and lack the degree of quantitative resolution necessary to easily permit measurement of effects of therapeutic intervention and degrees.

In recent years there have been a number of efforts to develop systems for detecting alertness and drowsiness by attempting to quantify the brain waves of a subject. Most of these systems have been aimed at the alertness monitoring field for alertness critical applications. Examples of these types of systems are as follows: Levin U.S. Pat. No. 6,167,298 discloses a device for monitoring and maintaining an alert state of consciousness for a subject wearing the device. With this device an alert mental state is maintained through monitoring of brain wave patterns to detect if a transition from an alert to a non-alert mental state is about to occur, or has occurred. If so, the device provides a stimulus until such time as an alert mental state, as assessed by the brain wave activity, is restored. Levendowski et al. U.S. Pat. No. 6,496,724 discloses a method of classifying individual EEG patterns along an alertness-drowsiness classification continuum. The results of the multi-level classification system are applied in real-time to provide feedback to the user via an audio or visual alarm, or are recorded for subsequent off-line analysis. Kaplan et al. U.S. Pat. No. 5,813,993 discloses an alertness and drowsiness detection and tracking system. The system claims improved performance by preserving and analyzing brain wave signal components at frequencies above 30 Hz.

Most of the methods, systems or devices currently on the market either provide a qualitative means for analyzing for excessive daytime sleepness or more specifically for sleep disorders, or a semi-quantitative means for classifying a subjects state of alertness. None of the above mentioned methods, systems or devices provide a quantitative means of measuring and determining whether an individual suffers from excessive daytime sleepiness and more specifically from a sleeping disorder, particularly one in which the analysis and measurement are capable of being provided in a short time duration and at low cost to the patient or insurance company. It is therefore an object of the present invention to provide a quantitative method of analysis wherein it can be determined whether a patient exhibits excessive daytime sleepiness based on a number or a quantitative profile of the patient exceeding a predetermined number or quantitative profile respectively over a given period of time. It is still another object of the present invention that this method be inexpensive and/or of short time duration. It is still another object of the present invention that a patient's therapeutic treatment can be more accurately determined based on the quantitative number or profile from the testing of the patient, and can subsequently be adjusted accordingly based on a subsequent test of the patient.

SUMMARY OF THE INVENTION

The present invention relates to a method of analyzing a subject for excessive daytime sleepiness, and more particularly to a quick (short duration), quantitative method of sleep disorder analysis. The present invention additionally relates to a method, which can be used to quantitatively measure the treatment endpoints for the subject's excessive daytime sleepiness, i.e., appropriate levels of stimulants.

There are numerous embodiments of the present invention, which are envisioned with a few of those listed below. The present invention relates to a method of analyzing a subject, and preferably a human subject for excessive daytime sleepiness and more preferably for sleeping disorders. These sleep disorders include but are not limited to narcolepsy, respiratory sleep disorders including obstructive sleep apnea, periodic limb movement disorder, restless leg syndrome, substance induced sleep disorders, dyssomnias, parasomnias, and sleep disorders related to a medical condition.

The method of sleep analysis of the present invention is generally and preferably of a short duration. This method represents a major cost savings for patients and their insurance company(s), and a major time savings for the patient and physician. This method can be used either as a screening test for sleep disorders, or as it gains more acceptability, as the primary method of diagnosing sleep disorders. Since this method is a quantitative one, the method allows the physician or trained technician to more easily determine the degree or level of the subject's disorder, and likewise provides another method of assessing the improvement of the subject after treatment or therapy, i.e., either physically or through medication.

The present invention further is related to a system used for the analysis. The system is potentially inexpensive and portable allowing for more extensive screening of the public for these types of disorders. This system could be used in a physician's office, or directly at the patient's home by the physician or trained technician.

In one embodiment, the present invention includes a method of analyzing a subject for sleep disorders over a test time period comprising the steps of determining that a subject has maintained a normal sleeping pattern prior to the analysis; using at least one sensor to measure the subject's brain wave signals over a measurement time period, the measurement time period comprising a number of time segments; analyzing the subject's brain wave signals to estimate or determine a number or a power spectrum profile for each time segment; and making a determination that the subject has a sleep disorder based in part on a computed number based on the number for each time segment over the measurement time period exceeding a predetermined threshold number, a profile of the numbers over the measurement time period exceeding a predetermined threshold profile over the time period, or the power spectrum profile exceeding a predetermined threshold power spectrum profile over the measurement time period. Optionally, this embodiment further includes the method wherein the subject's brain wave signals is transformed to a power spectrum, the power spectrum comprising an alpha component and one or more sub-alpha components, the subject's brain wave signals are analyzed to determine a ratio of the one or more sub-alpha components to the alpha component of the power spectrum, and the determination of whether the subject has a sleep disorder is based in part on an average of the ratio of the one or more sub-alpha components to the alpha component exceeding a predetermined threshold number or threshold profile over the measurement time period.

In another embodiment, the present invention includes a method of analyzing a subject for excessive daytime sleepiness over a test time period comprising the steps of using at least one sensor to measure a subject's brain wave signals over a measurement time period, the measurement time period comprising a number of time segments; analyzing the subject's brain wave signals to estimate or determine a power spectrum profile for each time segment of the measurement time period, the power spectrum comprising a alpha component and at least one sub-alpha component, and from these components a ratio of the one or more sub-alpha components to the alpha components for each time segment; and making a determination of the degree of excessive daytime sleepiness based in part on the ratio over the measurement time period.

In still another embodiment, the present invention includes a method of analyzing a subject for excessive daytime sleepiness over a test time period comprising the steps of using at least one sensor to measure a subject's brain wave signals over a measurment time period, the measurement time period comprising a number of time segments; analyzing the subject's brain wave signals to estimate or determine a number from the power spectrum of the brain wave signals in the from about 0 to about 30 Hz range or a power spectrum profile from the signal components from the brain wave signals in the from about 0 to about 30 Hz range for each time segment; and making a determination of the degree of excessive daytime sleepiness based in part on the number or the power spectrum profile for the time segments over the measurement time period wherein the measurement time period begins at least about 2 minutes after the test time period beings and wherein the test time period is less than about 60 minutes.

In still another embodiment, the present invention includes a method of analyzing a subject for sleep disorders comprising the steps of placing at least one sensor onto a subjects head having a brain wave signal; providing a stimulus to the subject; measuring the subject's response to the stimulus and the brain wave signal through the sensor; analyzing the brain wave signal; and making a determination that the subject has a sleep disorder based in part on the brain wave signal analysis over a measurement time period, and in part on the subject's response to the stimulus over a period of time.

In still another embodiment, the present invention includes a method of therapeutically treating a subject for sleep disorders comprising the steps of quantitatively analyzing a subjects brain wave signals and using the quantitative analysis in estimating or determining whether the subject has a sleeping disorder; making a physical change to the subject or giving the subject a medication to make an improvement to the subject's sleeping disorder based in part on the quantitative analysis; quantitatively analyzing a second time the subjects brain wave signals to estimate or determine the extent of the improvement to the subject's sleeping disorder; and, if necessary, making an additional physical change to the subject or reducing or increasing the medication in response to the previous step.

In still yet another embodiment, the present invention includes a system for analyzing sleep disorders of a subject comprising at least one brain wave sensor that measures brain wave signals; a component for delivering a stimulus to a subject; a component for response by the subject to the delivered stimulus; a processor or computer that analyzes the measured brain wave signals in relation to the stimulus to and response from the subject to determine whether the subject suffers from a sleeping disorder.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention, and together with the description serve to explain the principles and operation of the invention.

DESCRIPTION OF THE PREFERRED EMBODIMENT

Figure 1:
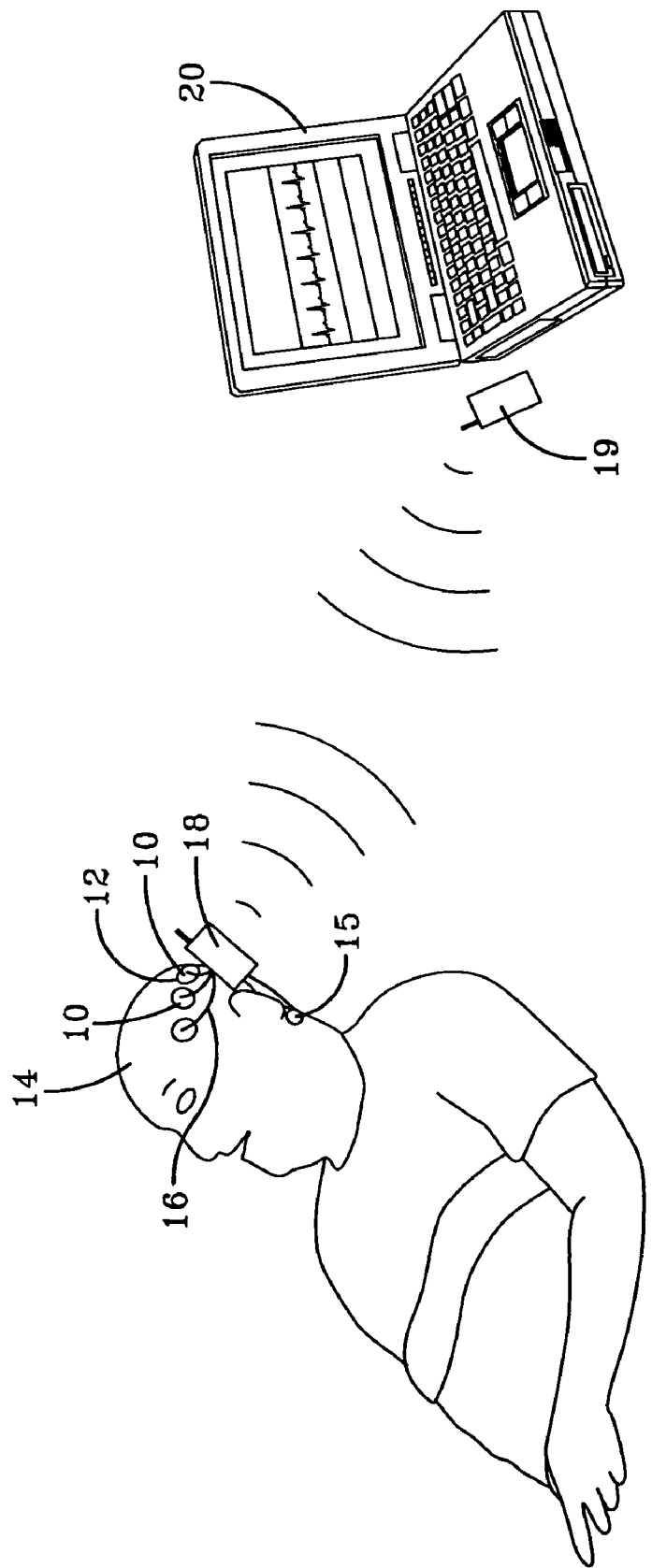
FIG. 1. is an illustration of a subject wearing a sensor to pickup and transmit brain wave signals to a computer for quantitatively analyzing the subject for excessive daytime sleepiness and/or sleep disorders.

The present invention relates to a method of analyzing a subject for excessive daytime sleepiness, and more particularly to a quick (short duration), quantitative method of sleep disorder analysis. The present invention also includes a sleep analysis system.

Various embodiments of the present invention include a step for determining whether the subject being analyzed for a sleep disorder maintained a normal sleeping pattern prior to the analysis. This step can be performed or accomplished a number of ways. In the simplest form, the subject can be questioned regarding his or her previous sleep patterns. In a somewhat more complex form the subject can be requested to fill out a questionnaire, which then can be graded to determine whether his or her previous sleep patterns where normal (or appeared normal). In an even more complex form the subject might undergo all night polysomnography to evaluate the subject's sleep architecture (e.g., obtaining respiratory disturbance index to diagnose sleep apnea). One of the objectives of this step is to ensure that the quantitative data results of the subject's brain wave analysis are not the result of or affected by the subject's previous environmental factors i.e., intentional lack of sleep, etc. It is clear that there are numerous ways beyond those examples previously mentioned of determining whether the subject being analyzed maintained or thought they were maintaining a normal sleeping pattern prior to analysis, therefore the examples given above are included as exemplary rather than as a limitation, and those ways of determining whether the subject maintained or thought they were maintaining a normal sleeping pattern known to those skilled in the art are considered to be included in the present invention.

The present invention involves the step of using at least one sensor to measure a subject's brain wave signals over a period of time. The brain wave or EEG signals can be obtained by any method know in the art, or subsequently developed by those skilled in the art to detect these types of signals. Sensors include but are not limited to electrodes or magnetic sensors. Since brain wave signals are, in general, electrical currents which produce associated magnetic fields, the present invention further anticipates methods of sensing those magnetic fields to acquire brain wave signals similar to those which can be obtained through for example an electrode applied to the subjects scalp. The subject(s) referred to in the present invention can be any form of animal. Preferably the subject(s) are mammal, and most preferably human.

If electrodes are used to pick up the brain wave signals, these electrodes may be placed at one or several locations on the subject(s)' scalp or body. The electrode(s) can be placed at various locations on the subject(s) scalp in order to detect EEG or brain wave signals. Common locations for the electrodes include frontal (F), parietal (P), anterior (A), central (C) and occipital (O). Preferably for the present invention at least one electrode is placed in the occipital position. In order to obtain a good EEG or brain wave signal it is desirable to have low impedances for the electrodes. Typical EEG electrodes connections may have an impedance in the range of from 5 to 10 K ohms. It is in general desirable to reduce such impedance levels to below 2 K ohms. Therefore a conductive paste or gel may be applied to the electrode to create a connection with an impedance below 2 K ohms. Alternatively, the subject(s) skin may be mechanically abraded, the electrode may be amplified or a dry electrode may be used. Dry physiological recording electrodes of the type described in U.S. patent application Ser. No. 09/949,055 are herein incorporated by reference. Dry electrodes provide the advantage that there is no gel to dry out, no skin to abrade or clean, and that the electrode can be applied in hairy areas such as the scalp. Additionally if electrodes are used as the sensor(s), preferably at least two electrodes are used— one signal electrode and one reference electrode; and if further EEG or brain wave signal channels are desired the number of electrodes required will depend on whether separate reference electrodes or a single reference electrode is used. For the various embodiments of the present invention, preferably an electrode is used and the placement of at least one of the electrodes is at or near the occipital lobe of the subject's scalp.

Now referring to FIG. 1, which is an illustration of a subject wearing a sensor to pickup and transmit brain wave signals to a computer for quantitatively analyzing the subject for excessive daytime sleepiness and/or sleep disorders. In FIG. 1 an electrode (sensor) 10 is placed on the central lobe 12 of the subject's scalp 14, and another reference electrode (sensor) 1.7 is placed behind the subject's ear 15. The electrodes 10 are dry electrodes. The electrodes 10 are releasable connected to leads 16 which can be connected to a processing unit (not shown) or to a wireless telemetry unit 18, which transmits the raw brain wave or EEG signal to a receiver 19 and then processing unit 20 for analysis. Not shown it is clear to someone skilled in the art where the placement of the electrode 10 will be required in order to maintain a close proximity between the electrode 10 and that portion of the brain. The number of electrodes 10 and likewise signals to be analyzed depends on the environment in which the sleep analysis system is to be used. In a more formal setting, it may be desirable to collect and analyze multiple brain wave or EEG signals from several locations on a subject's scalp. In a less formal setting such as a family practitioner's, internist's or general practitioner's office, it may be desirable to apply one sensor that requires little or no expertise in placement of the electrode, i.e., a dry electrode. The electrodes can preferably be placed in the locations of the frontal (F), parietal (P), anterior (A), central (C) and occipital (O) lobes of the brain.

Once the sensor(s) is in place relative to the subjects head in order to detect the subject's brain wave or EEG signal, the subject is preferably instructed to sit in a comfortable chair or lie down in a supine position. Further preferably, the subject is instructed to close their eyes throughout the test and relax, but to try and not fall asleep. The subject's brain wave or EEG signals are preferably recorded and analyzed during a test time period. The test time period is defined as the period of time in which the subject's brain waves signals are measured or recorded, and in general this corresponds closely to the time period in which the subject is hooked up to the quantitative, excessive daytime sleepiness measuring system. Generally, the test time period is preferably less than about 4 hours, more preferably less than about 2 hours, still more preferably less than about 60 minutes, still more preferably less than about 30 minutes, even still more preferably less than about 20 minutes, even still more preferably less than 15 minutes, and most preferably less than about 10 minutes. It has been found, generally, that a given amount of test time is necessary for a subject's brain wave signals to evolve into a consistent pattern. Therefore, the period of time in which brain waves are used for analysis preferably begins after this initial period of inconsistent data and is called the measurement time period. Preferably the measurement time period (also known as the time period over which the data is analyzed) begins at least 2 minutes after the test time period began, more preferably 4 minutes after the test time period began and most preferably 6 minutes after the test time period began. The measurement time period ends before or at the time the test time period ends.

Optionally the test may include the subject's response to one or more types of stimulus. Still further preferably, if this step, is included into the method, the subject is instructed to respond to certain types of the one or more stimulus. Still further preferably, the subject's response and lack of response are measured along with the timing of the subjects response relative to the stimulus. The stimulus provided to the subject can be based on any of the subject's senses including hearing, sight, smell, touch, or taste. Preferably, because the subject may be requested to close their eyes during the test (and given the types of stimuli devices currently readily available) the stimulus is based on the subject's sense of hearing or touch. More preferably, the stimulus is based on the subject's sense of hearing. In one particular embodiment of the subject's sensory response, a processor, such as a PC computer with specialized software, is used to generate a series of auditory tones for the subject. These auditory tones are further linked to the brain wave or EEG signals of the subject. With respect to the auditory tones, the subject could be instructed to listen for a particular tone (and respond in some way) and ignore the other tones. An example of this would be to generate a series of auditory tones in the form of phonemes such as "BA" or "GI". The volume level would be set low enough such that the subject would be able to comfortably hear the tone but not too loud to disturb or startle. These tones can be communicated to the subject either through ear phones or speakers. These tones would be generated by a program or software on a computer or processor respectively. For the duration of the test, the subjects would be instructed to listen for a particular tone and ignore other tones. Preferably, the tones are at least 1.5 seconds apart. In the preferred protocol, the subject will have to press a switch (e.g., a push-button) as soon as they hear a particular tone (e.g., BA) and ignore other types of tones (GI). For embodiments of the present invention, where the protocols involve pressing a push-button or other types of switches, preferably the subject practices a few times before the start of the test to become familiar with the feel and the handling of the switch. If the subject is unable or unwilling to press the switch, protocols can be used that do not require such a manual response.

During the test, the subject's response to the stimulus is preferably measured and the accuracy of the subject's response is evaluated preferably by a computer or processor by examining the status of the subject's response (through for example the switch identified in the one embodiment) following the onset of the stimulus (for example the auditory tones in the same embodiment). In the particular embodiment referred to the processor or computer would compute the time delay between the occurrence of the auditory stimulus and the time in which the switch is activated. If the subject manages to press the switch within the allowable interval immediately after the appropriate auditory stimulus (i.e., the tone for which the subject is instructed to respond), the analysis through the processor or computer assigns a correct response for that duration of the test. If, however, on the other hand the subject fails to respond or activates the switch when the stimulus was supposed to be ignored, the processor or computer assigns an incorrect response for that duration of the test. Preferably, the subject's reaction time and/or accuracy of response are used (in part) along with the analysis of the subject's brain waves to make a determination of whether the subject is suffering from a sleeping disorder. Furthermore, the subject's measured response can be used as an indicator as to whether the subject is cooperating with the test by comparing the measured response with the analyzed brain wave signals over the same time period.

During the testing of a subject for excessive daytime sleepiness or for a sleep disorder, preferably, the subject's brain wave or EEG signals are collected and analyzed to estimate or determine a number or power spectrum profile for each sampling moment or time segment. The signals can be collected through conventional recorders, analog signal processors or similar other devices and analyze after collection, however, given the easy access to digital technology such as processors and computers preferably the collection and analysis of the brain wave or EEG signals is carried out nearly concurrently (or simultaneously) using these digital means. In one embodiment of the present invention, a processor or computer receives digitized signals based on analog signals from the sensor used to measure the subject's brain wave or EEG signals. The sampled brain wave or EEG signals are then band-pass filtered in preferably the 0.1 Hz to 50 Hz range using a digital filter, e.g. a butterworth filter. This is followed by a first step of artifact detection and removal.

In the first step of analysis after data collection, the artifacts in the data are preferably identified and removed. In artifact detection and removal, the band-pass filtered data of the brain wave or EEG sample is compared with the standard deviation of the brain wave or EEG sample over the entire test or a portion of the test in which that sample is taken. If the brain wave or EEG sample is greater than some multiple of the standard deviation, preferably greater than about 3 times and more preferably greater than about 5 times, then that EEG sample is marked as an artifact and is replaced by a value that is derived from the artifact-free segment of the data immediately before. The artifact-free segment of data is that portion of the sampling data preferably greater than about 0.1 seconds before and also preferably less than about 0.6 before the artifact in sampling time.

This brain wave or EEG sample data is then preferably broken into consecutive sampling moments or time segments. These sampling moments or time segments are preferably 2 seconds in duration allowing for example 400 sampling points if the brain wave or EEG signal sampling rate was 200 samples per second. Each consecutive time segment is then transformed into a frequency domain representation (also known as power spectrum or frequency power spectrum) using techniques known to those skilled in the art. One technique, which is preferred, is to use a standard Fast Fourier Transform method (FFT). The FFT coefficients obtained are then squared and scaled to obtain the power spectrum plot (i.e., the power of brain wave or EEG signal at each frequency level). In this embodiment since the segment duration is for 2 seconds, the frequency resolution will be 0.5 Hz, and power values can be obtained for frequency bins of 0.5, 1, 1.5, 2, 2.5, . . . , 50 Hz.

The power spectrum of each time segment is used to determine if the time segment contains movements and other types of artifacts. Some of the artifacts manifest themselves in abnormally large power values in all frequencies, particularly at very low frequencies <10 Hz, compared to the power spectrum of the entire study. Upon detection of such abnormally high power spectra, preferably the entire sampling segment (in this embodiment 2 seconds) is marked as contaminated by the artifacts and is replaced by an average power spectrum of the artifact-free segments.

Brain wave data that is monitored and analyzed according to the present invention is between about 0.1 to about 50 Hz. Preferably, between 0.1 to about 30 Hz, more preferably between about 0.1 to about 15 Hz, and most preferably between about 0.1 to about 13 Hz. Also in certain embodiments of the present invention brain waves are categorized as delta, theta, alpha and beta waves or components. Delta waves or components generally exhibit brain wave or EEG activity in the frequency range from about 1 Hz to about 4 Hz, theta waves or components generally in the frequency range from about 6 Hz to about 7.5 Hz, alpha waves or components generally in the frequency range from about 7.5 Hz to about 13 Hz, and beta waves or components generally in the frequency range from about 13 Hz to about 30 Hz. As those skilled in the art will appreciate, the boundaries between these components are somewhat arbitrary. Thus, the foregoing delineations are intended to be exemplary and not limiting. Furthermore, use of other components, whether now known or later discovered, are within the scope of the invention.

In one embodiment of the present invention, the frequency power spectrum or power spectrum is used to determined a number for each sampling moment or time segment, and an average number over a measurement time period, which may include numerous sampling moments or time segments is determined. This number is then compared with a predetermined threshold number which has been calculated (and in a sense calibrated) based on previous tests using this technique on individuals with no known sleeping disorders, and individuals with a range of known sleeping disorders. In a more specific embodiment, a number is obtained by using only the frequency power spectrum or power spectrum data at frequencies below about 13 Hz. In this embodiment, data at frequencies below about 13 Hz is subjected to some form of mathematical manipulation such as being input into an algorithm. As those skilled in the art will appreciate, the weighting of data from the various frequency power spectrums or power spectrum may vary as well as the number of power spectrum frequencies or power spectrum used in order to magnify the quantitative resolution of this method. In an even more specific embodiment of this sleep analysis method, a number is obtained at least in part based upon the sum of the power in the 0.5–7.5 Hz frequency (and even more preferably in the 4–7.5 Hz frequency) bands divided by the sum of the power in the 7.5–13 Hz frequency bands (and more preferably in the 7.5–9.5 Hz frequency bands) to determine a ratio or an average number over a given measurement time period or period of time. This number is then compared with a predetermined threshold number which has been calculated (and in a sense calibrated) based on previous tests using this even more specific technique on individuals with no known sleeping disorders, and individuals with a range of known sleeping disorders.

In another embodiment of the present invention, the frequency power spectrum or power spectrum is used to determine a profile of the subjects a sampling data over a period of time or measurement time period. The period of time or measurement time period for the profile may either be the entire testing period, some portion thereof, which may include numerous sampling moments or time segments. This profile is then compared with a predetermined threshold profile which has been determined based on previous tests using this technique on individuals with no known sleeping disorders, and individuals with a range of known sleeping disorders (or based on what is determined to be a typical profile for someone with no known sleeping disorder or for an individual with a specific sleeping disorder). In another more specific embodiment, a profile is obtained by using only the frequency power spectrum or power spectrum data at frequencies below about 13 Hz. In this more specific embodiment, data at frequencies below about 13 Hz is subjected to some form of mathematical manipulation such as being input into an algorithm to form the profile. As those skilled in the art will appreciate, the weighting of data from the various power spectrum frequencies may vary as well as the number of power spectrum frequencies or power spectrum used. In an even more specific embodiment of this sleep analysis method, a profile is obtained over a period of time equal to all or part of the test that at least in part based upon the sum of the power in the 0.5–7.5 Hz frequency (and even more preferably in the 4–7.5 Hz frequency) bands divided by the sum of the power in the 7.5–13 Hz frequency bands to determine an average number over a given period of time or measurement time period. This frequency power spectrum or power spectrum data is then plotted over time to create a profile for the subject over the measurement time period. This profile is then compared with a predetermined profile which has been determine based on previous tests using this same even more specific technique on individuals with no known sleeping disorders, and individuals with a range of known sleeping disorders (or based on what is determined to be a typical profile for someone with no known sleeping disorder or for an individual with a specific sleeping disorder).

In addition to the above techniques, many other methods of analyzing the data can be used to further enhance the resolution of the data between subjects and to eliminate any noise in the analyzed data. It is envisioned that the present invention includes those techniques and any other techniques know to those skilled in the art.

Figure 2:
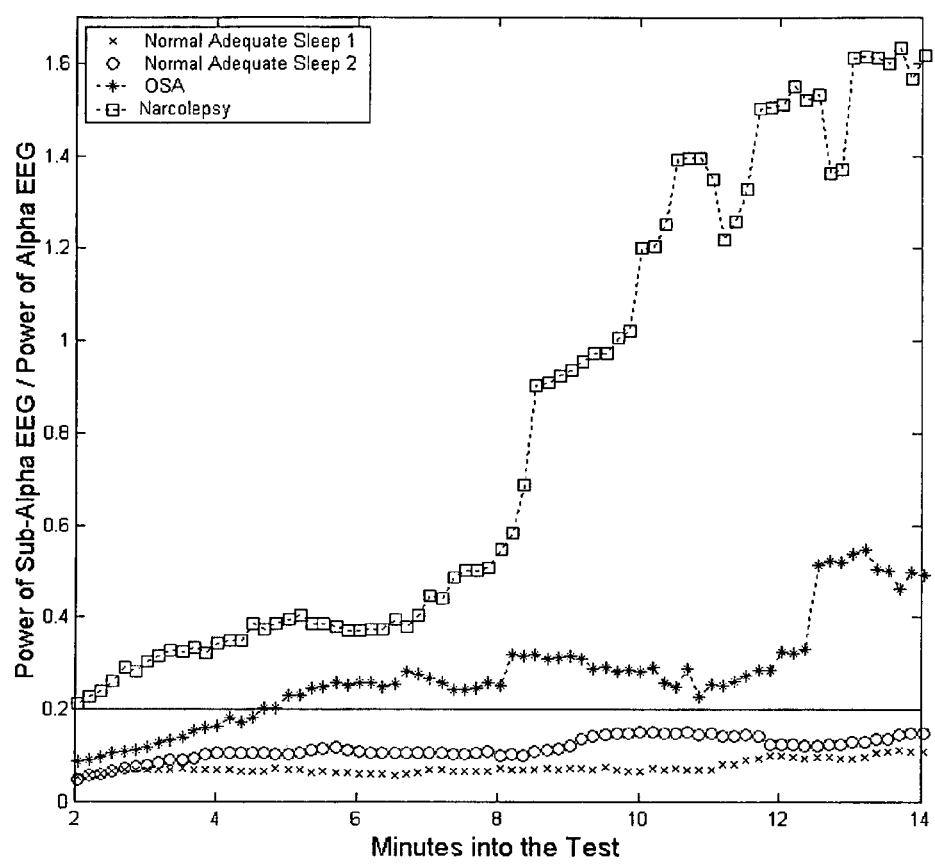
FIG. 2. is a graph showing a comparison of a number of subjects' profiles with a threshold profile to determine whether the subjects suffer from a sleeping disorder.
Figure 3:
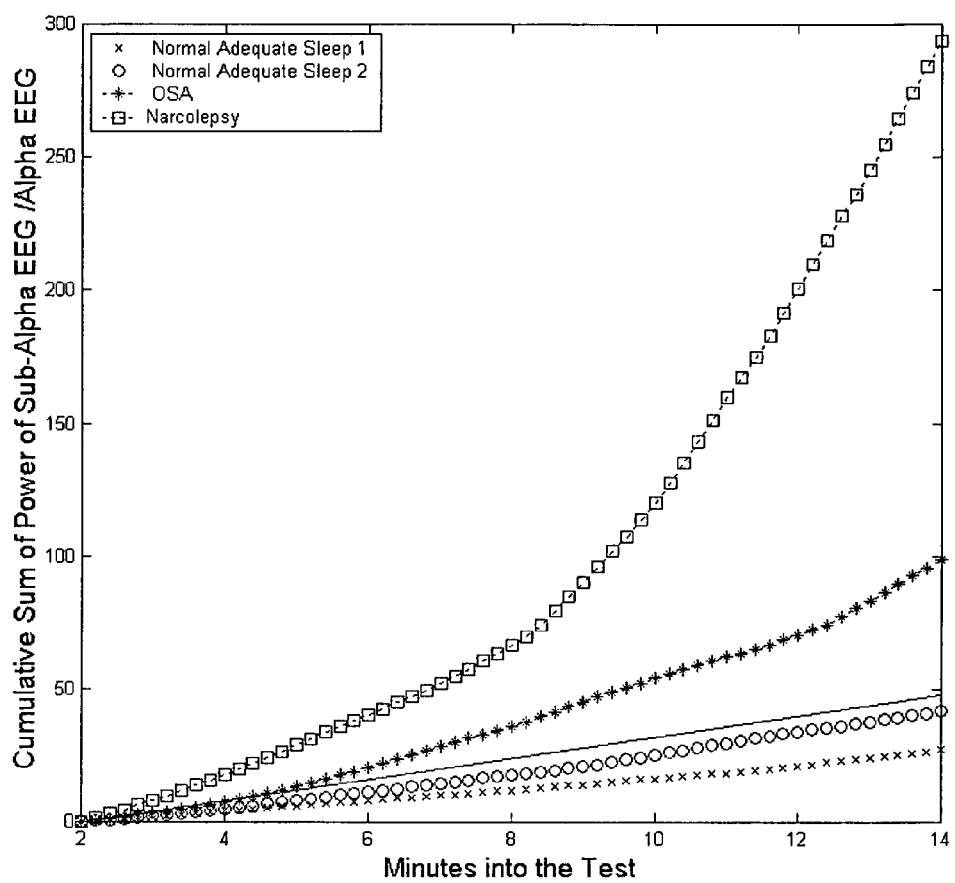
FIG. 3. is another graph showing a comparison of the a number of subjects' cumulative profiles with a threshold cumulative profile to determine whether the subjects suffer from a sleeping disorder.

FIGS. 2 and 3 show the frequency power spectrum or power spectrum profiles resulting from the measurement and analysis of a subject's brain wave signals over a measurement time period. The data was collected using a number of EEG electrodes applied to a subject for the measurement time period. The data was then analyzed with a computer processor to determine a number for each time segment. The measurement time period in both of these FIG.'s is the same as or very similar to the test time period. The number for each time segment was then plotted over the measurement time period to create a profile for the subject. For both of the FIG.'s, it is clear that two of the profiles quantitatively indicate that the subject has a sleeping disorder given that the subject's profile exceeds a predetermined threshold profile over the measurement time period (which can also be something less than the test time period).

Although not shown, the analyzed data generated for the FIG.'s can also be used to create a number for each time segment. The number for each time segment can be used by itself, or an average over the time segments can be used, or another number can be computed based on the number for each time segment. This number for the subject can be used in part to compare over the measurement time period to a predetermined threshold number to determine whether the subject suffers from a sleeping disorder or excessive daytime sleepiness.

Also not shown, the power spectrum profiles for each time segment can be plotted over the measurement time period to create a profile for the subject. This profile can then be compared with a predetermined threshold power spectrum profile to determine whether the subject suffers from a sleeping disorder or excessive daytime sleepiness.

FIG. 2 is a graph which is based on analysis of different subject's brain waves. In FIG. 2 a number was calculated from the subject's power spectrum data for each time segment over the measurement time period, and is one embodiment showing a quantitative profile comparison. In FIG. 2, the sub-alpha power spectrum data were divided by the alpha power spectrum data to give the ratio index or number referred to by the y-axis. The horizontal line 100 in the graph represents the threshold profile where if the number based on the subject's power spectrum data for each time segment exceeds or substantially exceeds the threshold profile then the subject suffers from excessive daytime sleepiness or a sleeping disorder. It is clear from the graph that two of the subjects 110 and 112 do not exceed this threshold profile. It is also evident that one of the subjects 120 which suffered from sleep apnea exceeded the profile substantially over the measurement time period, and after approximately 5 minutes into the measurment time period exceeded the threshold profile. It is also clear that the other subject 130 that suffered from narcolepsy exceeded the threshold profile over the entire measurment time period.

FIG. 3 is another graph which is based on analysis of different subject's brain waves. In FIG. 3, a number was calculated from the subject's power spectrum data for each time segment over a measurement time period, and is another embodiment showing a quantitative profile comparison. In FIG. 3, the sub-alpha power spectrum data were divided by the alpha power spectrum data to give the ratio index or number and this ratio index or number was cumulatively calculated over the measurement time period. The straight sloped line 200 in the graph represents the threshold profile where if the number from subject's power spectrum data for each time segment exceeds or substantially exceeds the threshold profile over the measurement time period, then it is determined that the subject suffers from excessive daytime sleepiness or a sleeping disorder. It is also evident that one of the subjects 220 which suffered from sleep apnea exceeded the profile substantially over the test period, and after approximately 5 minutes into the measurement time period exceeded the threshold profile. It is also clear that the other subject 230 that suffered from narcolepsy exceeded the threshold profile over the entire measurement time period.

In another embodiment of the present invention, the methods described above are used to therapeutically treat a subject for sleeping disorders, this being a new method unto itself. In this embodiment, the subject's brain wave signals are quantitatively analyzed to determine if the subject has a sleeping disorder as described above by indexing or profiling the subject, or by some other method that henceforth becomes known to those skilled in the art. If the subject is found to have a sleeping disorder; a physician, technician or veterinarian therapeutically treats the subject by either making a change in either the physical sleeping conditions of the subject or by giving the subject a medication to make an improvement to the subject's sleeping disorder. The subject is then re-tested by quantitatively analyzing the subject's brain wave signals to estimate or determine the extent of improvement of the subject's sleeping disorder after some reasonable period of time to allow for the therapy to have its effect. Then if based on the results of the re-test the subject is found to have fully improved no further steps are necessary. If, however, the subject is determined to have a quantitative number or profile which still varies from a normal subject (what is determined to be a quantitative number or profile for a subject with no sleeping disorders), a decision can be had to increase or reduce the therapeutic treatment or to add additional therapies to get alignment of the subject's quantitative number or profile with that of a normal subject. The alternating of the testing and therapeutic treatment possibly could have a number of iterations. It is, however, believed that as this process is refined that a physician for example will be able to review the subject's quantitative number or profile along with other physical characteristics of the subject such as weight, etc and very accurately determine the type of therapeutic treatment that will be necessary, and that at this point only a small number of subject's will need to have their therapy readjusted.

The present invention not only includes the above methods of quantitatively diagnosing a subject for sleep disorders and the further therapeutic treatment of the subject, but also a monitor or system for diagnosing sleep disorders. The monitor or system comprises a brain wave sensor that measures brain wave signals; a component for delivering a stimulus to a subject; a component for response by the subject to the delivered stimulus; a processor or computer that analyzes the measured brain wave signals in relation to the stimulus to and response from the subject.

The sensor for the monitor or system is the same as that described for use in the above methods. The sensor is designed to feed the brain wave or EEG signals through either leads or a wireless telemetry system into a processor or computer.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

What is claimed:

1. A method of analyzing a subject for sleep disorders over a test time period comprising the steps of:
    a) determining that a subject has maintained a normal sleeping pattern prior to the analysis;
    b) using at least one sensor to measure the subject's brain wave signals over a measurement time period, the measurement time period comprising a number of time segments;
    c) analyzing the subject's brain wave signals to estimate or determine a number or a power spectrum profile for each time segment; and
    d) making a determination that the subject has a sleep disorder based in part on a computed number based on the number for each time segment over the measurement time period exceeding a predetermined threshold number, a profile of the numbers over the measurement time period exceeding a predetermined threshold profile over the time period, or the power spectrum profile exceeding a predetermined threshold power spectrum profile over the measurement time period.

2. The method in claim 1, wherein the subject's brain wave signals are analyzed to estimate or determine a power spectrum profile for each time segment comprising an alpha component and one or more sub-alpha components, and a ratio of the one or more sub-alpha components to the alpha component for each time segment, and the determination of whether the subject has a sleep disorder is based in part on the ratio over the measurement time period.

3. The method in claim 2, wherein the sensor measures EEG signals from the subject's brain.

4. The method in claim 3, further including a step of providing one or more types of stimulus to the subject.

5. The method in claim 4, wherein the subject is instructed to respond after recognizing one or more of the types of the stimulus.

6. The method in claim 5, further including the step of measuring the subject's response to the one or more types of stimulus and wherein the stimulus is provided on an intermittent basis.

7. The method in claim 6, wherein the determination that the subject has a sleep disorder is further based in part on the subject's response to the one or more types of stimulus.

8. A method of analyzing a subject for excessive daytime sleepiness over a test time period comprising the steps of;
    a) using at least one sensor to measure a subject's brain wave signals over a measurement time period, the measurement time period comprising a number of time segments;
    b) analyzing the subject's brain wave signals to estimate or determine a power spectrum profile for each of the time segments of the measurement time period, the power spectrum for each time segment comprising an alpha component and at least one sub-alpha component, and from these components a ratio of the one or more sub-alpha components to the alpha components for each time segment; and
    c) making a determination of the degree of excessive daytime sleepiness based in part on the ratio of the over the measurement time period.

9. The method in claim 8, wherein the sensor measures EEG signals from the subject's brain.

10. The method in claim 9, further including a step of providing one or more types of stimulus to the subject.

11. The method in claim 10, wherein the subject is instructed to respond after recognizing one or more of the types of the stimulus.

12. The method in claim 11, further including the step of measuring the subject's response to the one or more types of stimulus and wherein the stimulus is provided on an intermittent basis.

13. The method in claim 12, wherein the determination that the subject has a sleep disorder is further based in part on the subjects response to the one or more types of stimulus.

14. The method in claim 8, wherein the measurement time period begins at least about 2 minutes after the test time period beings and wherein the test time period is less than about 60 minutes.

15. A method of analyzing a subject for sleep disorders comprising the steps of:
    a) placing electrodes onto a subjects head having a brain wave signal;
    b) providing a stimulus to the subject;
    c) measuring the subject's response to the stimulus and the brain wave signal;
    d) analyzing the brain wave signal; and
    e) making a determination that the subject has a sleep disorder based in part on the brain wave signal analysis over a period of time, and in part on the subjects response to the stimulus over the period of time.

16. The method in claim 15, wherein the stimulus is one or more auditory stimulus.

17. The method in claim 16, wherein the measured brain wave signal is filtered before analyzing.

18. The method in claim 17, wherein the stimulus is provided on an intermittent basis.

19. The method in claim 18, wherein a power spectrum profile is estimated or determined for each time segment of the analyzed brain wave signal, the power spectrum profile comprising an alpha component and one or more sub-alpha components and a ratio is calculated of the one or more sub-alpha components to the alpha component.

20. The method in claim 19, wherein the determination that the subject has a sleep disorder is based in part on an average of the ratio of the one or more sub-alpha components to the alpha component either exceeding a predetermined threshold number over a period of time or a profile of the ratio over a period of time.

* * * * *